(12) United States Patent
Suermondt et al.

(10) Patent No.: US 7,051,009 B2
(45) Date of Patent: May 23, 2006

(54) AUTOMATIC HIERARCHICAL CLASSIFICATION OF TEMPORAL ORDERED CASE LOG DOCUMENTS FOR DETECTION OF CHANGES

(75) Inventors: Henri Jacques Suermondt, Sunnyvale, CA (US); Melchun Hsu, Los Altos Hills, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 701 days.

(21) Appl. No.: 10/113,318

(22) Filed: Mar. 29, 2002

(65) Prior Publication Data
US 2003/0187809 A1    Oct. 2, 2003

(51) Int. Cl.
G06G 7/00    (2006.01)
G06N 5/00    (2006.01)
G06N 5/02    (2006.01)
G06F 17/00   (2006.01)

(52) U.S. Cl. .............................. 706/20; 706/45; 706/46
(58) Field of Classification Search .................. 706/46, 706/20, 50; 707/6
See application file for complete search history.

(56) References Cited

U.S. PATENT DOCUMENTS

| | | | |
|---|---|---|---|
| 6,233,575 B1 * | 5/2001 | Agrawal et al. | 707/6 |
| 2002/0022956 A1 * | 2/2002 | Ukrainczyk et al. | 704/9 |
| 2003/0130993 A1 * | 7/2003 | Mendelevitch et al. | 707/3 |

* cited by examiner

Primary Examiner—Anthony Knight
Assistant Examiner—Ronald E Williams, Jr.

(57) ABSTRACT

A method and apparatus for automatic detection of trends (and epidemics) among cases faced by a customer or patient support organization, based on automated classification of the logs of those cases in a topic hierarchy. The method includes establishing an item topic hierarchy of desired granularity and applying that hierarchy to a selected group of items, automatically classifying new items to at least one topic in the hierarchy, establishing windows having sequential sets of items based upon selected temporal parameters, determining item distributions over respective windows, and comparing respective item distributions in at least two such windows.

20 Claims, 2 Drawing Sheets

AUTOMATIC HIERARCHICAL CLASSIFICATION OF TEMPORAL ORDERED CASE LOG DOCUMENTS FOR DETECTION OF CHANGES

BACKGROUND OF THE INVENTION

1. Field of the Invention

This invention generally relates to a hierarchical classifier to detect trends in a temporally ordered set of cases, and more particularly to the continuous, complete, automated monitoring of changes in frequencies of hierarchical topics of cases including, for example, medical cases of patient problems or business-related case of customer service requests.

2. Discussion of the Related Art

Technology exists that can be used to automatically categorize items such as documents into a hierarchy of possible categories or topics. Some such existing technology is based on the manual authoring of rules, e.g., "if the document contains the word [database] then put it in the category 'databases'". Alternatively, fully automated methods to do such categorization exist, for example, based on level-by-level Bayesian categorization, or based on C4.5. It is believed that applications to automatically aggregate and analyze the results of such categorization over multiple sets of items or over multiple time windows are not presently known. The current state of the art is that such analysis would have to be done manually, for example by a business analyst into reports.

The closest known prior art applies a hierarchical classifier to documents recently accessed to determine which support documents are most used by customers. This tool considers only the distribution within a single (the recent) time window. This information can then also be used as a proxy to detect which topics are most frequently the cause of customer problems.

How things are distributed, for example, trends up or down for anything, can provide very useful and important information if the information can be assembled, handled, classified and analyzed properly.

SUMMARY OF THE INVENTION

The invention allows the automatic detection of trends including sudden dramatic changes (such as epidemics) among cases faced by a customer or patient support organization, for example, based on automated classification of the logs of those cases in a topic hierarchy. For example, customer complaints may be collated and analyzed to determine trends so that management decisions can be made for adjustments that result in fewer bases for such complaints. Another example is to determine trends in retail sales.

This invention could apply in any situation (in addition to customer or patient support) where:

1) documents are generated in a way that induces temporal ordering;
2) documents can be classified automatically into a topic hierarchy or some other form of categorization;
3) trends or changes in the distribution of these documents across the topic hierarchy constitute useful information.

An embodiment of the invention is a method for detecting trends for a temporally ordered set of items by establishing a item topic hierarchy of desired granularity and applying that hierarchy to the items by automatically classifying items to at least one topic in the hierarchy, establishing sets of items based upon selected temporal parameters, determining item distributions for each set of items, and comparing respective distributions in at least two sets of items.

Various embodiments of the invention may have the sets of items overlapping or non-overlapping. The method could have an output related to which topics are changing in relative frequency, especially where there is a sudden or substantial change, or which topics are no longer needed. The invention, in some embodiments, can determine the nature of changes in topic frequencies, or whether there is a need to alter the topic hierarchy. Trends among topics can be detected by comparing item distributions for a set of items over an extended period of time in some embodiments. In an alternative embodiment the invention can compute a measure of the total degree of change among item distributions. The output of the apparatus and method may be in any desired form of perception, audio or visual, or any combination of audio or visual forms.

BRIEF DESCRIPTION OF THE DRAWING

The aforementioned objects and advantages of the present invention, as well as additional objects and advantages thereof, will be more-fully understood hereinafter as a result of a detailed description of a preferred embodiment, when taken in conjunction with the following drawing, in which.

DETAILED DESCRIPTION OF THE PREFERRED EMBODIMENTS

Figure 1:
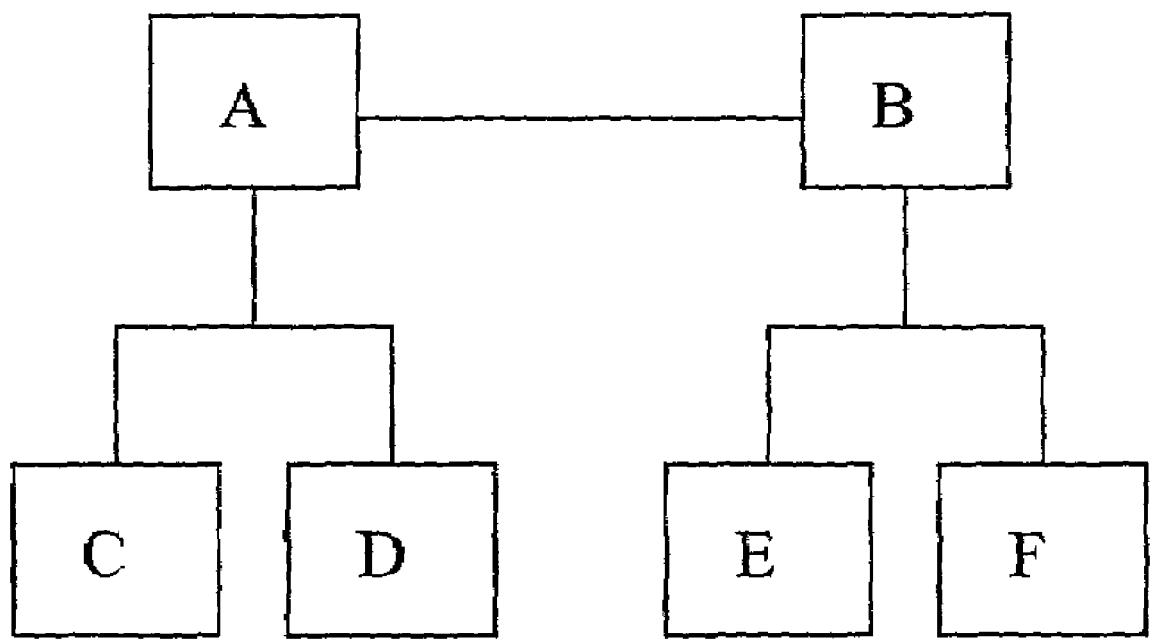
FIG. 1 is simplified hierarchical topic array used to illustrate certain aspects of the invention.

In one embodiment, this invention uses a hierarchical classifier to detect trends in a temporally ordered set of cases or case log documents. The information provided by the invention can be employed to make decisions in any situation where case or item matters can be collected, classified and analyzed to show changes or trends.

Cases handled by a customer support organization, for example, are commonly documented in case log documents. Each case log commonly documents the case to a varying degree of completeness. A case log can contain the presenting problem (that is, what the customer noticed), results of diagnostic questions by support technicians, actions taken, and the final solution to or resolution of the problem. A case log can consist of a single document, or of a collection of documents, which form a logical unit.

Cases occur at a particular time. Thus, in a support organization, one may see a stream of cases and the resulting case logs. These case logs can be considered in the order that they were generated or in some other appropriate time-based order. For example, such order for consideration could be based on the time that the problem was first noticed, based on the time that the support organization was first called, or based on the time when the product underlying the case was manufactured or purchased, among others. Such an ordering of cases and case logs can be referred to as the temporal case ordering. The ordering, for the purposes of this invention, does not have to be complete, as long as it is possible to select a group of documents that more or less refer to the same time period or window. For example, all cases can be aggregated for a particular month, without caring how the cases are ordered within that month.

The customer support organization would have a topic hierarchy that is applied to known problems and solution documents. This hierarchy, which currently consists of a "tree" of topics, but which can be any collection of multiple topics, contains nodes, such as topics or categories, that form a useful grouping of similar cases or problems. Of course, the optimal granularity of this topic hierarchy depends on what is considered useful by the organization that uses it. For example, the term "topic hierarchy" can be used to refer to such a collection of topics, organized in some manner to reflect super/subtopic relations.

Based on data mining and machine learning techniques, or based on manual authoring of classification rules, an automated or semi-automated classifier can be developed that can take as its input a document, such as a case log, and can assign it to one or more topics in the topic hierarchy. Such assignment of documents can be categorical or probabilistic, that is, a probability is generated that the document belongs to a category, or some combination of these. Such a classifier that assigns, in this manner, documents within a topic hierarchy, may be termed a hierarchical classifier.

A continuous window in the temporal case ordering is considered and it is observed how the cases in this window are distributed across the topic hierarchy. The window is a sequential set of cases or case logs taken from the temporal case ordering, with the possible omission of cases that are impossible to classify, atypical, or for some other reason should be left out.

The hierarchical classifier is applied to each of the cases (or case logs) from the window. By way of example, cases may be assigned categorically or probabilistically, and in one possible embodiment, cases may be assigned to multiple topics. From the total assignment of cases in the window using the classifier, a distribution of cases over the topic hierarchy can be derived. For example, it could be seen that 26% of the cases in the window are about topic "HP-UX->Databases->Oracle." In one embodiment, probabilistic information could be combined with the degree of assignment by the classifier to reach conclusions like "topic HP-UX-Patches-installation is supported by cases in this window to a degree of 13%." The totals may be in percentages, fractions, or other units of measurement. In one embodiment, the totals over all categories can be normalized, that is, made to sum up to 100% or 1. This normalization may happen across the entire hierarchy, or across one "level" in the hierarchy, or among all the children of any one node. One interpretation of the results of classification of cases in a window over the topic hierarchy is a set, or vector, of indicators that indicates the extent to which various topics are descriptive of the cases in the window.

Now that the distribution over the topic hierarchy of cases or case logs in a window can be computed, the distribution from one window can be compared to that from another. Note that the windows do not have to be the same length, or size (number of cases), although the conclusions may be more meaningful if the windows are sufficiently large to be representative. From such a comparison, which can take into account as well the time location of the window, conclusions can be drawn, such as:

1) which topics are changing in relative frequency;
2) which topics are no longer needed or occurring;
3) what sort of change are evident in the (relative) topic frequencies;
4) whether there is a substantial or a sudden dramatic increase in cases about a particular topic, for example, something like an epidemic;
5) whether there is a need to change the hierarchy, for example, because a topic is no longer sufficiently specific and therefore needs further refinement; or
6) using the hierarchy information, whether there is a shift in the distribution of cases among subtopics for a particular topic. For example, under the topic "operating system Win98," a shift of cases about subtopic set "office application problems" toward subtopic "modem problems" might be observed. Such information could be used, for example, to draw conclusions about the common usage of products underlying the cases.

The comparison among time windows can be based on two or more windows. The windows may be overlapping or non-overlapping. The comparability of windows may be taken into account when drawing the conclusions. For example, December 1999 vs. December 2000 may provide an indication of changes in holiday support needs; "last two weeks" vs. "the month before that" may show the latest changes and trends. The best selection of windows depends on the application. For example, to detect slow drift in the topic distribution, non-overlapping windows may be better. On the other hand, if it is important to detect a radical change as soon as possible, a sliding window compared to a reference window may be best.

The hierarchy allows conclusions to be drawn at different levels of granularity. Consider the example shown in FIG. 1. in one embodiment, topic A may encompass information about its subtopics C and D. At node A in the topic hierarchy, the total number of documents that belong to all the nodes below A are included. Thus, a big increase in relative frequency of topic A would provide aggregate information about the set of topics {A, C, D}, whereas a big change in C would only provide information about C itself. Thus, changes in relative frequency at various levels in the hierarchy provide information at different levels of granularity.

Figure 2:
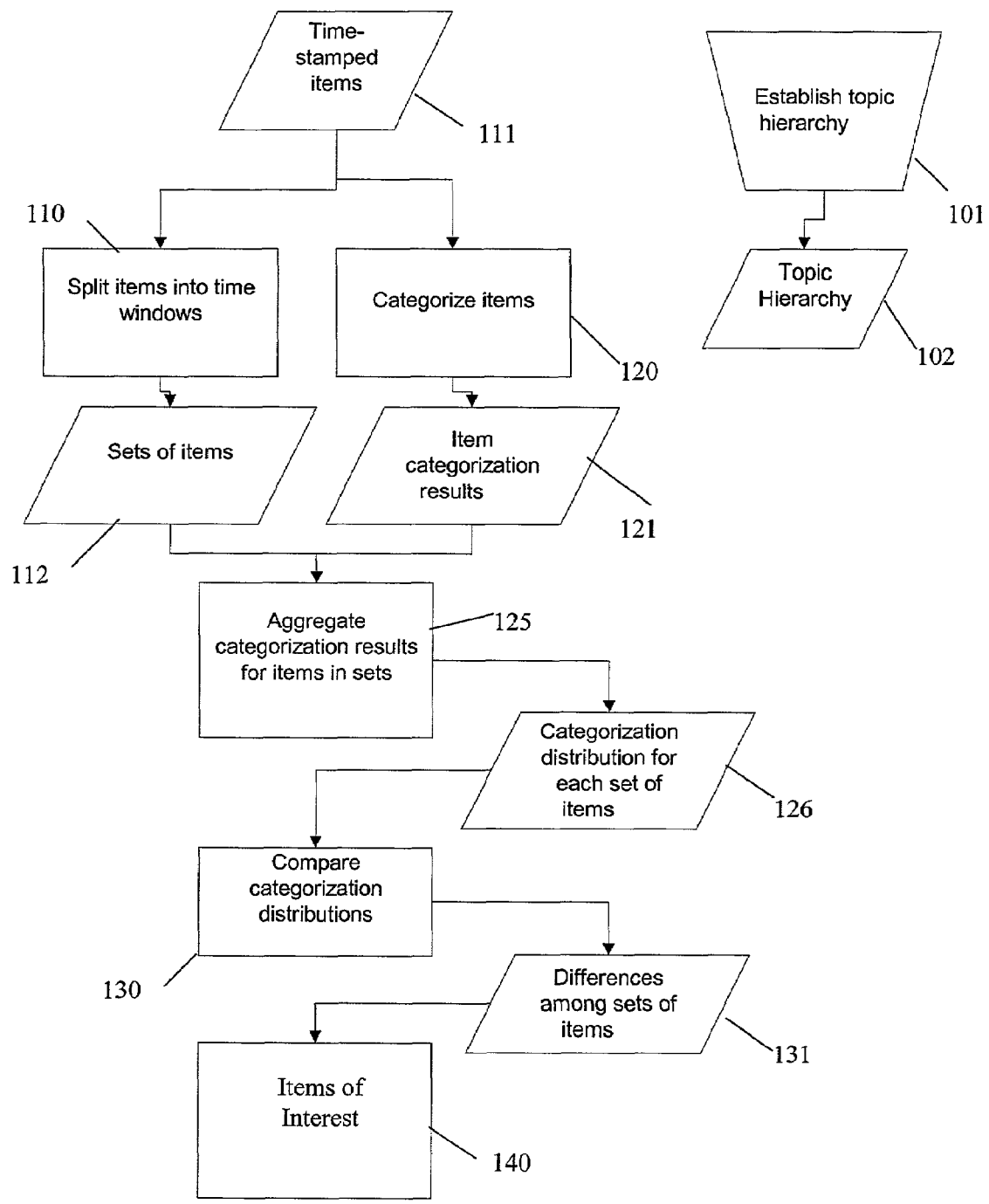
FIG. 2 is a block diagram of a preferred embodiment.

In an exemplary embodiment as illustrated in FIG. 2, in step 101 a person or organization manually generates an appropriate topic hierarchy 102 for the application of the invention. This may be done once in preparation (with the resulting topic hierarchy 102 saved for future reuse), or it may be done during each application of the invention. In an alternative embodiment, topic hierarchy 102 may also be obtained from an external source, such as a standards body or a government organization such as the National Library of Medicine. Provided with a collection of time-stamped items 111, such as, for example, customer-support logs or records representing patient-doctor visits, in step 110 time-stamped items 111 are divided into at least two sets of items 112. Step 110 can be performed by manually or automatically selecting one or more cut-off time stamps that represent which time-stamped items should go into which set. Alternatively, step 110 can be performed by manually selecting items for each set. In step 120, the same time-stamped items are categorized using known categorization technology, resulting in item categorization results 121. Such categorization technology can be used to automatically assign items to categories in a topic hierarchy 102, for example, using level-by-level naïve Bayes categorization or using technology such as that commercially available from Autonomy, Inc., having a place of business in San Francisco, Calif. The item categorization results 121 can be the assignment of one of more items to one or more categories in topic hierarchy 102. Next, in step 125, the item categorization results 121 are aggregated for each of the sets of items 112, resulting in a categorization distribution 126. Such a distribution can consist of a description as to which percentage of the items in each of sets 112 belong to one or more of the categories in topic hierarchy 102. In step 130, each such distribution 126 is compared to at least two of the sets of items 112. The result of step 130 is an analysis of differences 131 among the sets of items 112. In the preferred embodiment, such an analysis of differences 131 includes identification of categories that have seen significant increase or decrease in percentage of items that belong to them. Finally, in step 140, items from the analysis of differences 131 that may be of interest are output.

The output of the process shown in FIG. 2 may be visual, such as bar graphs, a printout, or a light or combinations of lights having pre-assigned meanings. The output may also be an image of the topic hierarchy 102 in which visual cues indicate which categories are experiencing large changes in relative frequency. The output could be audible, such as an alarm, or even an automated microprocessor-generated voice. Of course, the output could be both visual and audible.

The purpose of the outputs from the process or apparatus of the invention is to provide information about changes or trends that can be used in making important decisions. The invention incorporates at least one CPU which analyzes many inputs to arrive at the output information.

In another embodiment, changes to the topic hierarchy and in the corresponding hierarchical classifier can be taken into account. In that case, meaningful, albeit possibly partial, conclusions about trends among topics can be drawn, provided a mapping that indicates how the categories in one version of the hierarchy correspond to those in the other version(s) has or can be obtained. In that embodiment, the conclusions of the classifier for cases in a particular window can be stored, and at future times the stored conclusions can be compared to future window distributions, without having to re-apply the new classifier to old cases, even if the hierarchy or classifier changes (for example, if topics are added).

Another embodiment of this invention uses a visualization tool that allows one to show the changes in the distribution. For example, this tool could display the topic hierarchy and highlight topics that have seen a large (relative) increase or decrease, possibly in different colors.

Another alternative embodiment of the invention includes computing a summary measure, or set of measures, that indicates the degree of change to the distribution. In one embodiment, a statistical measure such as cross-entropy could be used for this purpose. Such a measure could then be combined with a threshold and used in an alerting manner: If the total change is significant, that is, it is greater than the threshold, then the user could be alerted that there is a notable change in the distribution across the topic hierarchy. Such a summary measure could also be generated for particular portions of the hierarchy. In the extreme case, a summary measure can be generated for each topic that indicates the relative significance of the change to that topic. For topics that have sub-topics (children), the summary measure may optionally include the degree of change to the children of the topic.

Having thus disclosed exemplary embodiments, it being understood that other variations and additions are contemplated and that the scope hereof is limited only by the appended claims and their equivalents.

What is claimed is:

1. A processor-based method for detecting developments among temporally ordered items, the method comprising:
   applying an item topic hierarchy of desired granularity in a processor-based system to said items by applying at least a partially automated classifier in the processor-based system to assign said items to at least one topic in the topic hierarchy;
   establishing at least two sets of said items based upon selected temporal parameters;
   determining the distribution of said items in said topic hierarchy for each of said sets of items;
   comparing respective distributions among at least two of said sets of items; and
   computing with the processor-based system a summary measure of total degree of change among said respective distributions, and providing an output indication based upon said summary measure.

2. The method recited in claim 1, wherein said sets of items are non-overlapping.

3. The method recited in claim 1, wherein said sets of items are overlapping.

4. The method recited in claim 1, and further comprising determining which topics are changing in relative frequency.

5. The method recited in claim 1, and further comprising determining which topics are no longer needed.

6. The method recited in claim 1, and further comprising determining the nature of changes in topic frequencies.

7. The method recited in claim 1, and further comprising determining whether there is a substantial increase in items relating to a particular topic.

8. The method recited in claim 1, and further comprising determining whether there is a need to alter the topic hierarchy.

9. The method recited in claim 1, and further comprising detecting trends among topics by comparing item distributions for one selected set of items over an extended period of time.

10. The method recited in claim 1, and further comprising providing a perceivable representation of the result of the comparing the respective distributions among the at least two of said sets of items.

11. A processor-based apparatus for detecting developments among temporally ordered items, the apparatus comprising:
    processor-based means for applying an item topic hierarchy of desired granularity to said items by applying a least a partially automated classifier that is processor-executed to assign said items to at least one topic in the topic hierarchy;
    means for establishing at least two sets of items based upon selected temporal parameters;
    means for determining the distribution of said items in said topic hierarchy for each of said sets of items;
    means for comparing respective distributions among at least two of said sets of items; and
    processor-based means for computing a summary measure of total degree of change among said distributions, and providing an output indication based upon said summary measure.

12. The apparatus recited in claim 11, wherein said sets of items are non-overlapping.

13. The apparatus recited in claim 11, wherein said sets of items are overlapping.

14. The apparatus recited in claim 11, and further comprising means for determining which topics are changing in relative frequency.

15. The apparatus recited in claim 11, and further comprising means for determining which topics are no longer needed.

16. The apparatus recited in claim 11, and further comprising means for determining the nature of change in topic frequencies.

17. The apparatus recited in claim 11, and further comprising means for determining whether there is a substantial increase in items relating to a particular topic.

18. The apparatus recited in claim 11, and further comprising means for determining whether there is a need to alter the topic hierarchy.

19. The apparatus recited in claim 11, and further comprising means for detecting trends among topics by comparing item distributions for one selected set of items over an extended period of time.

20. The apparatus recited in claim 11, and further comprising means for providing an audio-visual representation of comparing sets of items.

* * * * *

UNITED STATES PATENT AND TRADEMARK OFFICE
CERTIFICATE OF CORRECTION

| | | |
|---|---|---|
| PATENT NO. | : 7,051,009 B2 | Page 1 of 1 |
| APPLICATION NO. | : 10/113318 | |
| DATED | : May 23, 2006 | |
| INVENTOR(S) | : Henri Jacques Suermondt et al. | |

It is certified that error appears in the above-identified patent and that said Letters Patent is hereby corrected as shown below:

In column 6, line 42, in Claim 11, after "applying" delete "a" and insert -- at --, therefor.

Signed and Sealed this

Fifth Day of May, 2009

JOHN DOLL
*Acting Director of the United States Patent and Trademark Office*